United States Patent
Sorribas Amela et al.

(10) Patent No.: US 8,962,528 B2
(45) Date of Patent: Feb. 24, 2015

(54) PENOXSULAM AS AN HERBICIDE IN ALFALFA

(75) Inventors: Monica Sorribas Amela, Indianapolis, IN (US); Richard K. Mann, Franklin, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 108 days.

(21) Appl. No.: 13/433,712

(22) Filed: Mar. 29, 2012

(65) Prior Publication Data

US 2012/0252669 A1 Oct. 4, 2012

Related U.S. Application Data

(60) Provisional application No. 61/469,113, filed on Mar. 30, 2011.

(51) Int. Cl.
*A01N 43/90* (2006.01)
*A01N 25/32* (2006.01)
*A01N 43/60* (2006.01)

(52) U.S. Cl.
CPC ..................................... *A01N 43/90* (2013.01)
USPC ............................ 504/241; 504/105; 504/136

(58) Field of Classification Search
USPC ........................................ 504/105, 136, 241
See application file for complete search history.

(56) References Cited

U.S. PATENT DOCUMENTS

| | | | |
|---|---|---|---|
| 4,994,101 | A | 2/1991 | Young |
| 5,858,924 | A | 1/1999 | Johnson et al. |
| 5,965,490 | A | 10/1999 | Johnson et al. |
| 6,005,108 | A | 12/1999 | Johnson et al. |
| 6,130,335 | A | 10/2000 | Johnson et al. |
| 6,303,814 | B1 | 10/2001 | Johnson et al. |
| 7,820,595 | B2 | 10/2010 | Loughner et al. |
| 2004/0192556 | A1 | 9/2004 | Schregenberger et al. |
| 2010/0285959 | A1 | 11/2010 | Armel et al. |
| 2011/0098182 | A1 | 4/2011 | Mann et al. |
| 2012/0184435 | A1* | 7/2012 | Bristow ..................... 504/103 |

OTHER PUBLICATIONS

Childs, D, Common Chickweed Control in Alfalfa. [online]. Forages, Purdue University, 1992 [retrieved on May 20, 2013]. Retrieved from the Internet<http://www.agry.purdue.edu/ext/forages/publications/WS-18.htm> 3 pages.*

* cited by examiner

*Primary Examiner* — John Pak
*Assistant Examiner* — Andriae M Holt
(74) *Attorney, Agent, or Firm* — Michael R. Asam

(57) ABSTRACT

This invention concerns the use of penoxsulam as an herbicide in alfalfa.

10 Claims, No Drawings

PENOXSULAM AS AN HERBICIDE IN ALFALFA

CROSS REFERENCE TO RELATED APPLICATIONS

This application claims the benefit of U.S. Provisional Patent Application Ser. No. 61/469,113 filed Mar. 30, 2011, the entirety of which is incorporated herein by reference.

FIELD OF THE INVENTION

This invention concerns the use of penoxsulam as an herbicide in alfalfa.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. The present invention concerns a method of controlling undesirable vegetation in alfalfa with penoxsulam. Controlling weeds all year long is important in this perennial crop, as weeds compete with alfalfa for water, nutrients and sunlight. Weed control is important during the summer growing season to reduce weed competition and undesirable vegetation in the harvested crop, which is important when used for animal food and fodder. Weed control is important in the dormant period of alfalfa growth in order to maintain the alfalfa population and reduce weed competition for water, nutrients and sunlight. Weed control options in alfalfa are limited; therefore, a need for new herbicides in alfalfa exists.

The herbicide compound forming the composition of this invention is known in the art for its effect as an herbicide.

SUMMARY OF THE INVENTION

The present invention concerns a method of controlling undesirable vegetation in alfalfa which comprises contacting the undesirable vegetation or the locus thereof with an herbicidal amount of penoxsulam. Alfalfa has been shown to be tolerant to penoxsulam in the dormant period.

DETAILED DESCRIPTION OF THE INVENTION

Penoxsulam is the common name for (2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in *The Pesticide Manual*, Fifteenth Edition, 2009. Penoxsulam controls barnyardgrass, as well as many broadleaf and sedge weeds in aquatics, rice, turf, tree nut and vineyard crops, cereal and grain crops, and IVM.

The term herbicide is used herein to mean an active ingredient that kills, controls or otherwise adversely modifies the growth of plants without adversely affecting the crop. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

In general, the composition of the invention can be applied at an application rate of between about 8.8 grams penoxsulam per hectare (g ai/ha) and about 100 g ai/ha, preferably between about 35 g ai/ha and about 70 g ai/ha or between about 17.5 g ai/ha and about 70 g ai/ha.

The present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the present invention include: 2,4-DB, benfluralin (benefin), bentazon, bromoxynil, clethodim, diuron, EPTC, ethafluralin, fluazifop, flumioxazin, glyphosate, halosulfuron, hexazinone, imazamox, imazethapyr, metribuzin, norflurazon, oxyfluorfen, paraquat, pendimethalin, pronamide, sethoxydim, terbacil and trifluralin.

Penoxsulam can further be used in conjunction with 2,4-D, glyphosate, glufosinate, dicamba or imidazolinones on 2,4-D tolerant, glyphosate-tolerant, glufosinate-tolerant, dicamba-tolerant or imidazolinone-tolerant alfalfa.

The composition of the present invention can generally be employed in combination with other known herbicide safeners, such as benoxacor, benthiocarb, brassinolide, cloquintocet (mexyl), cyometrinil, cyprosulfamate, daimuron, dichlormid, dicyclonon, dietholate, dimepiperate, disulfoton, fenchlorazole-ethyl, fenclorim, flurazole, fluxofenim, furilazole, harpin proteins, isoxadifen-ethyl, mefenpyr-diethyl, mephanate, MG 191, MON 4660, naphthalic anhydride (NA), oxabetrinil, R29148 and N-phenylsulfonylbenzoic acid amides, to enhance selectivity.

While it is possible to utilize the compound of the present invention directly as an herbicide, it is preferable to use it in mixtures containing an herbicidal amount of the compound along with at least one agriculturally acceptable adjuvant or carrier. Suitable adjuvants or carriers should not be phytotoxic to alfalfa, particularly at the concentrations employed in applying the compositions for weed control, and should not react chemically with the compounds or other composition ingredients. Such mixtures can be designed for application directly to alfalfa or its locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank-mixed.

Suitable agricultural adjuvants and carriers that are useful in preparing the herbicidal activity of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxanemethyl cap; nonylphenol ethoxylate+urea ammonium nitrate; emulsified methylated seed oil; tridecyl alcohol (synthetic) ethoxylate (8EO); tallow amine ethoxylate (15 EO); and PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono-, di- and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The concentration of the active ingredients in the composition of the present invention is generally from 0.001 to 98 percent by weight. Concentrations from 0.01 to 90 percent by weight are often employed. In compositions designed to be employed as concentrates, the active ingredients are generally present in a concentration from 1 to 98 weight percent, preferably 5 to 90 weight percent. Such compositions are typically diluted with an inert carrier, such as water, before application. The diluted compositions usually applied to alfalfa generally contain 0.0001 to 5 weight percent active ingredient and preferably contain 0.001 to 0.1 weight percent.

The present compositions can be applied to alfalfa or their locus by the use of conventional ground or aerial dusters, sprayers, and granule applicators, by addition to irrigation water, and by other conventional means known to those skilled in the art.

EXAMPLES

Evaluation of Herbicidal Tolerance to Alfalfa in the Field

A field trial (California) was conducted in field-grown alfalfa using standard herbicide small plot research methodology. Plots were 7.5 ft by 20 ft long with 4 replicates per treatment. The alfalfa crop was already established the previous season and was grown using normal cultural practices for fertilization, seeding, watering, and maintenance to ensure good growth of the crop.

All treatments in the field trials were applied using a $CO_2$ backpack sprayer calibrated to apply 187 L/ha spray volume. Commercially available product of penoxsulam was mixed in water at appropriate formulated product rates to achieve the desired rates based on a unit area of application (hectare). Treatments were sprayed as a postemergence application to the soil when alfalfa was in the late dormant stage of growth. "Late dormant" growth stage is defined as when the crop is not actively growing during the winter season and just prior to emerging from dormancy and starting new growth for the growing season. Treatments were rated at 26 to 63 days after the application as compared to the untreated control plants, when the alfalfa crop was no longer dormant. Visual crop injury ratings were scored on a scale of 0 to 100 where 0 corresponds to no injury and 100 corresponds to complete control.

Results

Table 1 demonstrates alfalfa growth tolerance results following an application of penoxsulam to dormant alfalfa. % Visual Regrowth is a visual evaluation of the growth of the dormant alfalfa after it comes out of dormancy in the spring. The "Untreated" treatment at the time of the first evaluation (26DAAA (Days After Application A timing)) demonstrates the growth of the alfalfa with no herbicide applied, and a rating of 71.3% is an average across the replicates of the % of the ground covered by alfalfa growth. All of the penoxsulam treatments demonstrated no significant difference in alfalfa regrowth as compared to the Untreated. % Visual Regrowth at 49DAAA demonstrates no significant difference in alfalfa regrowth from any penoxsulam treatment as compared to the Untreated (77.5%). % Visual Injury at 49DAAA demonstrates some slight visual injury of the alfalfa to all penoxsulam treatments compared to the Untreated, but this injury is minor and cosmetic. There is no effect on alfalfa growth as evidenced by the 63DAAA % Visual Regrowth evaluations which demonstrate no effect of any penoxsulam treatment on alfalfa growth as compared to the Untreated.

Table 2 demonstrates the significant weed control activity of penoxsulam on all weeds at the trial location at 45DAAA as compared to the untreated control. Penoxsulam provided 100% control of the two broadleaf weeds (STEME (chickweed) and CAPBP (Sheperd's purse)) based on the burndown and/or residual activity when rated at 45DAAA. Penoxsulam provided significant suppression/partial control of the grass weed POAAN (annual bluegrass) dependent on the rate applied earlier in the dormant alfalfa. This level of weed control is important to alfalfa growers, since weed competition in the early season of growth can reduce yield by competition for water, nutrients and sunlight.

These results demonstrate the commercially acceptable tolerance of alfalfa to dormant applications of penoxsulam, and the commercially acceptable weed control of key broadleaf and grass weeds provided by penoxsulam application in dormant alfalfa in California.

TABLE 1

Alfalfa tolerance to penoxsulam when applied as a late dormant, early growth stage in the spring, as compared to an untreated control and several other commercial standards.

| Treatment Number | Treatment Name | Rate | Rate Unit | Regrowth % Visual 26DAAA | Regrowth % Visual 49DAAA | Injury % Visual 49DAAA (1) | Regrowth % Visual 63DAAA (1) |
|---|---|---|---|---|---|---|---|
| | | | | Treatment to Evaluation Interval: | | | |
| 1 | UNTREATED | | | 71.3 a | 77.5 ab | 0 d | 95.7 a |
| 2 | PENOXSULAM | 17.5 | gr/ha | 76.3 a | 97.5 a | 2.5 c | 100 a |
| | AGRI-DEX COC | 2.34 | L/ha | | | | |
| 3 | PENOXSULAM | 35 | gr/ha | 43.8 a | 82.5 ab | 5 b | 97.5 a |
| | AGRI-DEX COC | 2.34 | L/ha | | | | |
| 4 | PENOXSULAM | 70 | gr/ha | 67.5 a | 83.8 ab | 10 a | 95 a |
| | AGRI-DEX COC | 2.34 | L/ha | | | | |

(1) = yellowing

TABLE 2

Efficacy of Penoxsulam Applied in Dormant Alfalfa.

| Treatment No. | Treatment Name | Rate | Rate Unit | Application Method | Application Timing | POAAN Control % Visual 45 DAAA | STEME Control % Visual 45 DAAA | CAPBP Control % Visual 45 DAAA |
|---|---|---|---|---|---|---|---|---|
| 1 | UNTREATED | | | | | 0 c | 0 b | 0 b |
| 2 | PENOXSULAM | 35 | gr/ai/ha | POST | NOV/JAN | 65 b | 100 a | 100 a |
| | AGRI-DEX COC | 2.33 | liter/ha | POST | NOV/JAN | | | |
| 3 | PENOXSULAM | 70 | gr ai/ha | POST | NOV/JAN | 79 ab | 100 a | 100 a |
| | AGRI-DEX COC | 2.33 | liter/ha | POST | NOV/JAN | | | |
| 4 | PENOXSULAM | 140 | gr ai/ha | POST | NOV/JAN | 91 a | 100 a | 100 a |
| | AGRI-DEX COC | 2.33 | liter/ha | POST | NOV/JAN | | | |

POAAN = *Poa annua*, annual bluegrass
STEME = *Stellaria media*, chickweed
CAPBP = *Capsella bursa-pastoris*, Shepherd's purse

What is claimed is:

1. A method of controlling undesirable vegetation in alfalfa comprising contacting the undesirable vegetation or locus thereof with an herbicidal effective amount of penoxsulam when the alfalfa is in the late dormant stage of growth, wherein the herbicidal effective amount of penoxsulam is applied at a rate of from 17.5 grams penoxsulam per hectare to 70 grams penoxsulam per hectare; wherein the alfalfa is tolerant to the application of the herbicidal effective amount of penoxsulam and no herbicide safener is applied to the alfalfa, undesirable vegetation, or locus thereof.

2. The method of claim 1, wherein the penoxsulam is contacted with soil.

3. The method of claim 1, wherein the penoxsulam is mixed with one or more agriculturally acceptable adjuvants or carriers.

4. The method of claim 3, wherein the one or more adjuvants or carriers is a crop oil concentrate, nonylphenol ethoxylate, benzylcocoalkyldimethyl quaternary ammonium salt, blend of a petroleum hydrocarbon, an alkyl ester, an organic acid, and an anionic surfactant, $C_9$-$C_{11}$ alkylpolyglycoside, phosphated alcohol ethoxylate, natural primary alcohol ($C_{12}$-$C_{16}$) ethoxylate, di-sec-butylphenol EO-PO block copolymer, polysiloxane-methyl cap, nonylphenol ethoxylate and urea ammonium nitrate, emulsified methylated seed oil, tridecyl alcohol ethoxylate, tallow amine ethoxylate, or PEG400 dioleate-99.

5. The method of claim 1, wherein the undesirable vegetation or locus thereof is contacted with one or more additional herbicides.

6. The method of claim 5, wherein the one or more additional herbicide is 2,4-DB, benfluralin, bentazon, bromoxynil, clethodim, diuron, EPTC, ethafluralin, fluazifop, flumioxazin, glyphosate, halosulfuron, hexazinone, imazamox, imazethapyr, metribuzin, norflurazon, oxyfluorfen, paraquat, pendimethalin, pronamide, sethoxydim, terbacil or trifluralin.

7. The method of claim 1, wherein the undesirable vegetation is *poa annua, stellaria media*, or *capsella bursa-pastoris*.

8. A method of controlling undesirable vegetation in alfalfa comprising contacting the locus of alfalfa with an herbicidal effective amount of penoxsulam when the alfalfa is in the late dormant stage of growth, wherein the herbicidal effective amount of penoxsulam is applied at a rate of from 17.5 grams penoxsulam per hectare to 70 grams penoxsulam per hectare; wherein the alfalfa is tolerant to the application of the herbicidal effective amount of penoxsulam and no herbicide safener is applied to the alfalfa, undesirable vegetation, or locus thereof.

9. The method of claim 8, wherein the penoxsulam is mixed with one or more agriculturally acceptable adjuvants or carriers.

10. The method of claim 8, wherein the undesirable vegetation is *poa annua, stellaria media*, or *capsella bursa-pastoris*.

* * * * *